United States Patent
Su et al.

(10) Patent No.: US 9,606,036 B2
(45) Date of Patent: Mar. 28, 2017

(54) METHOD FOR DETERMINING GEOMECHANICAL PARAMETERS OF A ROCK SAMPLE

(71) Applicant: TOTAL SA, Courbevoie (FR)

(72) Inventors: Kun Su, Pau (FR); Edmond Poyol, Pau (FR)

(73) Assignee: TOTAL SA, Courbevoie (FR)

( * ) Notice: Subject to any disclaimer, the term of this patent is extended or adjusted under 35 U.S.C. 154(b) by 103 days.

(21) Appl. No.: 14/391,978

(22) PCT Filed: Mar. 29, 2013

(86) PCT No.: PCT/FR2013/050699
§ 371 (c)(1),
(2) Date: Oct. 10, 2014

(87) PCT Pub. No.: WO2013/153311
PCT Pub. Date: Oct. 17, 2013

(65) Prior Publication Data
US 2015/0068292 A1   Mar. 12, 2015

(30) Foreign Application Priority Data
Apr. 12, 2012   (FR) ..................................... 12 53391

(51) Int. Cl.
*G01N 3/46*   (2006.01)
*G01N 3/42*   (2006.01)
(Continued)

(52) U.S. Cl.
CPC .................. *G01N 3/46* (2013.01); *G01N 3/42* (2013.01); *G01N 29/07* (2013.01); *G01N 33/24* (2013.01);
(Continued)

(58) Field of Classification Search
CPC ........................................................ G01N 3/46
See application file for complete search history.

(56) References Cited

U.S. PATENT DOCUMENTS 2,182,235 A   12/1939   Polushkin
3,876,251 A * 4/1975   Boyd ...................... E21C 37/16
                                                                299/1.1
(Continued)

FOREIGN PATENT DOCUMENTS

DE   199 50 310 A1   4/2001
JP   62 032340 A   2/1987
(Continued)

OTHER PUBLICATIONS

Mahabadi O K et al: "A novel approach for 1-11 micro-scale characterization and modeling of geomaterials incorporating actual material heterogeneity", Geophysical Research Letters 2812 American Geophysical Union USA, vol. 39, No. 1, Jan. 6, 2812 (2812-81-86), XP882689941, DOI: 18.1829/ 2811GL858411.
(Continued)

*Primary Examiner* — Ryan Walsh
(74) *Attorney, Agent, or Firm* — Patterson Thuente Pedersen, P.A.

(57) ABSTRACT

The present invention relates to a method for determining geomechanical parameters of a rock sample, including a searching step, during which the horizontal and vertical forces provided to a blade advancing at a constant speed and at a constant cutting depth along the sample are measured, in order to destroy a constant volume per unit of length at the surface of the rock sample; a micro-indentation step, during which mechanical features of the rock are determined by micro-indentation; a step of determining the geological parameters of the sample, during which at least one parameter chosen from the uniaxial compressive strength, the angle of friction, internal cohesion, Brinell hardness and
(Continued)

Young's modulus of the rock is estimated by means of measurements taken during the scratching and micro-indentation steps.

13 Claims, 1 Drawing Sheet

(51) Int. Cl.
 *G01N 33/24* (2006.01)
 *G01N 29/07* (2006.01)
(52) U.S. Cl.
 CPC ............... *G01N 2291/0232* (2013.01); *G01N 2291/0421* (2013.01); *G01N 2291/0422* (2013.01)

(56) References Cited

U.S. PATENT DOCUMENTS

| | | | | |
|---|---|---|---|---|
| 4,911,002 A * | 3/1990 | Enderlin | ............ | G01N 3/40 125/13.01 |
| 5,323,648 A * | 6/1994 | Peltier | ............ | E21B 49/006 436/28 |
| 5,670,711 A * | 9/1997 | Detournay | ............ | E21B 49/003 73/152.09 |
| 5,866,807 A | 2/1999 | Elings | | |
| 5,868,030 A * | 2/1999 | Brumley | ............ | G01B 5/30 73/784 |
| 6,155,104 A * | 12/2000 | Suresh | ............ | G01N 3/42 73/789 |
| 6,349,595 B1 * | 2/2002 | Civolani | ............ | E21B 49/005 73/152.02 |
| 6,941,819 B1 * | 9/2005 | Maki, Jr. | ............ | G01N 29/07 73/788 |
| 8,234,912 B2 * | 8/2012 | Suarez-Rivera | ............ | G01N 3/46 73/78 |
| 2005/0283985 A1 | 12/2005 | Yang et al. | | |
| 2006/0171579 A1 * | 8/2006 | Lee | ............ | G01N 3/42 382/141 |
| 2007/0151340 A1 | 7/2007 | Hsu et al. | | |
| 2011/0015907 A1 * | 1/2011 | Crawford | ............ | G01V 99/00 703/2 |
| 2012/0059590 A1 * | 3/2012 | Ameen | ............ | G01N 3/58 702/11 |
| 2012/0080123 A1 * | 4/2012 | Padula, II | ............ | C22F 1/18 148/508 |
| 2015/0136388 A1 * | 5/2015 | Fehr | ............ | E21B 33/1285 166/250.1 |

FOREIGN PATENT DOCUMENTS

| | | |
|---|---|---|
| RU | 2367923 | 9/2009 |
| RU | 2435955 | 12/2011 |
| WO | WO 01/25597 A1 | 4/2001 |

OTHER PUBLICATIONS

A-T. Akono et al: "Scratching as a Fracture Process: From Butter to Steel", Physical Review Letters, vol. 106, No. 20, May 1, 2011 (May 1, 2011), XP055048664, ISSN: 0031-9007, DOI: 10.1103/PhysRevLett.106.204302.

PCT International Search Report for International Application No. PCT/FR2013/050699, mailed Jul. 26, 2013, 3 pgs.

* cited by examiner

METHOD FOR DETERMINING GEOMECHANICAL PARAMETERS OF A ROCK SAMPLE

RELATED APPLICATIONS

The present application is a National Phase entry of PCT Application No. PCT/FR2013/050699, filed Mar. 29, 2013, which claims priority from FR Patent Application No. 12 53391, filed Apr. 12, 2012, said applications being hereby incorporated by reference herein in their entirety.

FIELD OF THE INVENTION

The present invention relates to a method for determining geomechanical parameters of a rock sample, and a device for implementing such a measurement method.

BACKGROUND OF THE INVENTION

During the geomechanical study of a subsurface, cores are conventionally collected from the subsurface in order to acquire rock samples.

The determination of certain geomechanical parameters of the rocks provides insight into the behavior of the underground structure when considering exploitation of the subsurface.

Some of these geomechanical parameters, such as the angle of friction ($\Phi$) or the cohesion (C) of the Mohr-Coulomb criterion that characterizes the failure threshold of the rock, are parameters used in all geomechanical studies at different scales, for example for a well, reservoir, cover, or oil field.

Usually, determination of the angle of friction and cohesion of a rock requires triaxial compression tests at different confining pressures.

Although they provide satisfactory results, these triaxial compression tests are complex to carry out, particularly for shale because of the cracks caused by drilling and storage (dehydration). In addition, these tests take a very long time, at least a week per test.

There is therefore a need for a method for determining geological parameters from a rock sample, including the angle of friction and cohesion of the rock, that is simpler and faster to implement than existing methods.

SUMMARY OF THE INVENTION

The invention thus provides a method for determining geomechanical parameters of a rock sample, comprising:
- a step of scratching a groove, during which the horizontal and vertical forces provided to a blade advancing at a constant speed and constant cutting depth along the surface of a sample are measured,
- a micro-indentation step, on the groove, during which mechanical properties of the rock are determined by micro-indentation,
- a step of determining geological parameters of the sample, during which at least one parameter chosen from among the uniaxial compressive strength, angle of friction, internal cohesion, Brinell hardness, and Young's modulus of the rock is estimated by means of measurements taken during the scratching and micro-indentation steps.

Advantageously, the method according to the invention provides an effective and non-destructive method for determining geomechanical parameters of the rock, including the angle of friction and cohesion.

Advantageously, the method according to the invention allows a rapid, non-destructive determination requiring only small amounts of rock sample.

Furthermore, the method according to the invention can be applied in a more or less continuous manner.

A method according to the invention may further comprise one or more of the following optional features, individually or in any combination:
- the method may further comprise a step of measuring acoustic parameters of the sample and wherein the Poisson's ratio of the rock is determined during the step of determining geomechanical parameters of the sample,
- the acoustic parameters include the propagation velocities of the compression and shear waves,
- the microseismic signals produced during the scratching and micro-indentation are recorded by a plurality of sensors placed on the rock sample and on the test bench,
- the measurements of micro-indentation and/or acoustic parameters are made within the groove created during the scratching step,
- the angle of friction ($\Phi$) and the cohesion (C) of the rock sample are determined based on interpretation of the inflection point of the micro-indentation force-displacement curve and the scratch forces,
- the rock sample is in the form of a core and the steps of measurement and of determining the geomechanical parameters of the sample are repeated along the sample length, and/or
- the sample is photographed during the measurement steps.

The invention also relates to a computer program product comprising a set of instructions which, when loaded into a computer, causes said computer to execute the steps of the method according to the invention.

The invention further relates to a device for measuring geomechanical parameters of a rock sample, said device comprising:
- a test bench intended for receiving a rock sample,
- a gantry whose movement along the sample is controlled and comprising micro-indentation and scratching instruments,
- a computer controlling the movement of the gantry along the sample, configured to receive the data measured by the instruments attached to the gantry and comprising calculation means which use the data received to determine at least one parameter among: the uniaxial compressive strength, angle of friction, internal cohesion, Brinell hardness, and Young's modulus of the rock sample.

According to one aspect of the invention, the gantry of the device further comprises an instrument for measuring acoustic parameters of the rock sample, and the computer of the device is configured so that it also receives the data measured by the instrument for measuring acoustic parameters and further comprises calculation means which allow using the received data to determine the Poisson's ratio of the rock sample.

BRIEF DESCRIPTION OF THE DRAWINGS

The invention will be better understood by reading the following description, provided purely by way of example and with reference to the accompanying drawings, in which.

For reasons of clarity, the various elements represented in the figures are not necessarily to scale.

DESCRIPTION OF PREFERRED EMBODIMENTS

Figure 1:
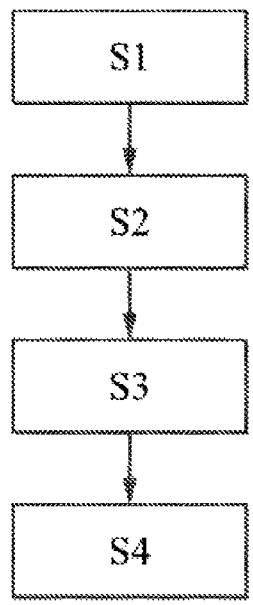
FIG. 1 represents the different steps of a method according to one embodiment of the invention.

In one embodiment, represented in FIG. 1, the method according to the invention comprises:
- a groove scratching step S1,
- a micro-indentation step S2,
- a step of measuring acoustic parameters S3, and
- a step of determining geomechanical parameters of the sample S4.

Figure 2:
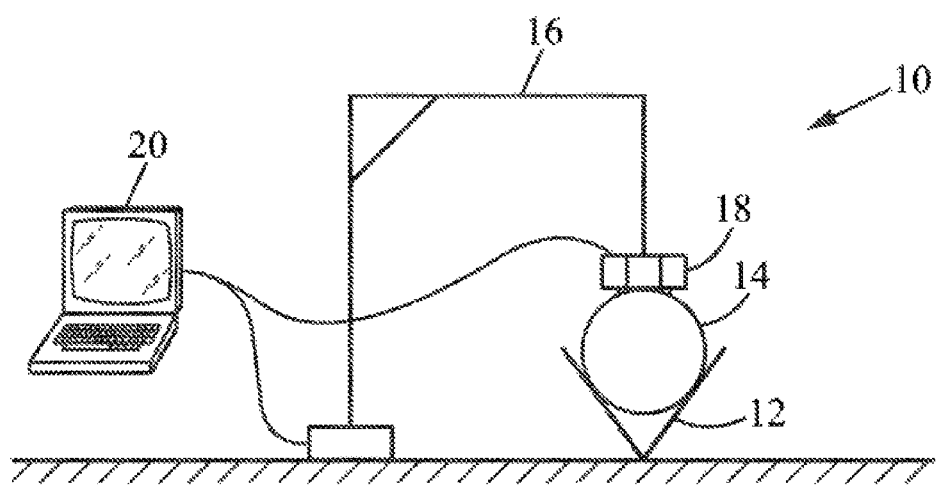
FIG. 2 is a schematic representation of a measurement device according to one embodiment of the invention.

Preferably, the method according to the invention is implemented by means of a device as represented in FIG. 2.

Such a device comprises:
- a test bench intended for receiving a rock sample, typically the V-shaped bench conventionally used for scratch tests,
- a gantry whose movement along the sample is controlled and comprising at least the micro-indentation and scratch test instruments 18, and possibly an instrument for measuring acoustic parameters of the rock sample,
- a plurality of sensors for capturing microseismic emissions, placed on the sample and on the bench.
- a computer 20 controlling the movement of the gantry along the sample and configured to determine geomechanical parameters of the rock sample, from the data measured by the instruments of the gantry. In addition, it records the signals of microseismic emissions during the measurements.

During the groove scratching step S1, the horizontal and vertical forces required to advance the blade, for example a cutter blade, at a constant speed and constant cutting depth along the sample in order to destroy a constant volume per unit of length at the surface of the rock sample, are measured.

The groove scratching step in the sense of the invention concerns a well-known test commonly referred to as the scratch test.

Interpreting these measurements in the context of an energy/volume approach allows estimating the profile of the intrinsic specific energy (ISE) along the length of the sample.

According to one embodiment, the advancement speed of the blade may be between 5 mm/s and 25 mm/s, and the cutting depth may vary between 0.05 mm to 0.5 mm depending on the type of rock analyzed and other aspects.

Because of surface irregularities, several prior passes may be required in order to obtain a flat surface along the core.

The values of the cutting forces at the blade-rock interface are recorded along the sample length at several depths which remain constant for the entire length of the groove.

During the micro-indentation step, the force-displacement characteristics of the sample are determined by micro-indentation.

According to one embodiment, the micro-indentation test is performed by means of a cylindrical or spherical indenter having a diameter of between 0.5 and 3 mm. The test can be performed at regular or irregular intervals on the surface of the groove created during the scratching step in order to measure the elastic properties and fracture parameters of the rock.

As the micro-indentation test is conducted by accessing the sample via the groove created during the scratching step, this provides a fresh rock surface, meaning a rock surface having properties closer to those of a rock not yet extracted. Data collected on this fresh rock surface are more relevant than data collected on a surface that has been exposed to ambient air.

According to a preferred embodiment of the invention, the piston of the indenter equipped with a load cell is also mounted on the gantry. The raising and lowering of the indenter occur automatically. The differential displacements of the indenter relative to the surface of the rock are measured using three sensors, for example LVDT sensors, one attached near the indenter and the other two attached to the gantry.

The force and displacement are recorded by the computer 20. The measurement increment can be varied as needed, for example a measurement increment of between 5 to 10 cm.

During the step S3 of measuring acoustic parameters, the acoustic parameters of the rock sample are measured. In particular, the propagation velocities of the compression waves $V_P$ and shear waves $V_S$ are measured during the step of measuring acoustic parameters.

According to a preferred embodiment of the invention, the propagation velocity measurements are performed on the surface exposed by the scratching step and within the micro-indentation test intervals.

According to one embodiment of the invention, after the passage of the blade during the scratching step, a smooth groove (surface) is obtained on the rock sample. The gantry 16 returns to its starting position.

The acoustic measurements are conducted using a transmitter and receiver placed in the groove that are separated by a predetermined distance, for example between 2 and 10 cm, in particular about 5 cm. The raising and lowering of the acoustic sensors can be done automatically with an arm installed on the gantry 16 and managed by the computer 20. Constant pressure is applied to the sensors to ensure good contact at the rock-sensor interface. The advancement increment for the measurements is constant, for example equal to the predetermined distance between the transmitter and receiver. In particular, the advancement increment can be equal to 5 cm.

Detection of micro-seismic emissions is achieved using a plurality of sensors placed directly on the core and on the test bench.

During the step of determining geomechanical parameters of the sample S4, the measured data are sent to the computer 20 which processes them to determine the geomechanical parameters.

The inventors have found that grouping these three measurements on one bench and coupling their interpretation allows characterizing multiple mechanical parameters of the rock simultaneously.

The elastic properties of the rock can be determined by micro-indentation: the Young's modulus (E) of the rock at the millimetric scale can be determined by analyzing the linear phase of the force-displacement curve obtained at each measurement point.

The uniaxial compressive strength (Rc) can be determined during the scratching step, using the empirical relationship between the intrinsic specific energy ($\xi$) and the strength Rc (fracture resistance under simple compression) obtained for samples of the same type of rock. During the scratching step, the profile of Rc can be obtained all along the core. The variability of the mechanical strength at the millimetric or metric scale can be characterized.

Plasticity parameters, including the angle of friction ($\phi$) and internal cohesion (C), can be determined using the coupled interpretation of data measured during the scratching step and micro-indentation step. The frictional force at the rock-blade interface as well as the force corresponding to the inflection point of the force-displacement curve of the micro-indentation and the non-linear phase of this curve are used to determine these parameters.

The linear portion of the force-displacement curve of the cylindrical indenter is used to calculate the elastic modulus (E).

The inventors propose making use of both the specific energy ($\xi$) provided by the scratch, and the force ($F_R$) and displacement ($e_R$) of the point of loss of linearity (R) of the force-displacement curve of the cylindrical indenter, to determine the angle of friction and the cohesion of the rocks.

The inventors propose making use of the microseismic emissions to interpret the different phases of the force-displacement curve of the micro-indentation and the impact of the cutting depth on the measurement of the specific energy of the scratching.

The inventors propose measuring the Brinell hardness of a rock sample with a spherical indenter by performing a cycle of applying/releasing the test force. The irreversible displacement measured after releasing the force is used to calculate the Brinell hardness number (HB).

Mechanical and acoustic data obtained on the same core surface allow establishing reliable correlations between the parameters. Such correlations serve to construct geomechanical logs for bore holes.

The effect of grouping measurements on a single bench minimizes the scattering of results caused by sample preparation, and additionally offers the possibility of coupling the interpretation of data originating from different measurements in order to obtain consistent mechanical parameters.

Advantageously, the method according to the invention is very effective in determining the fracture parameters of rocks, particularly clays as one of the major difficulties with clays is obtaining non-fissured samples.

The method of the invention can be applied to small samples, which offers a wide field of application in geomechanical studies (for example wellbore and cover stability) where the parameters of the failure criterion are often unknown because of a lack of samples suitable for conventional tests.

In addition, the micro-indentation test can be conducted directly on the cores. Values can therefore be obtained for cohesion C, angle of friction $\Phi$, Brinell hardness, and Young's modulus E at regular intervals along a certain core length.

A geomechanical log can thus be established, and can be extrapolated to the entire formation using correlations with the other logs recorded for the bores. This log is therefore input data for the modeling of hydraulic fracturing.

The embodiments above are intended to be illustrative and not limiting. Additional embodiments may be within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

The invention claimed is:

1. A method for determining mechanical parameters of a rock sample, comprising:
    scratching a groove in the rock sample by causing a blade to advance at a constant speed and constant cutting depth along the rock sample in order to destroy a constant volume per unit of length at the surface of the rock sample;
    measuring horizontal and vertical forces provided to the blade while scratching the groove;
    performing a micro-indentation test on the rock sample within the groove created by scratching the rock sample;
    determining mechanical properties of the rock sample while performing the micro-indentation test, and
    determining geomechanical parameters of the rock sample, comprising determining at least one parameter chosen from among uniaxial compressive strength, angle of friction, internal cohesion, Brinell hardness, and Young's modulus of the rock sample using measurements taken while scratching the groove and while performing the micro-indentation test.

2. The method according to claim 1, wherein determining mechanical parameters of the rock sample comprises determining the uniaxial compressive strength, angle of friction, internal cohesion, Brinell hardness, and Young's modulus of the rock sample using measurements taken while scratching the groove and while performing the micro-indentation test.

3. The method according to claim 2, wherein the rock sample is in the form of a core, the method comprising repeating the measurements taken while scratching the groove and while performing the micro-indentation test along the rock sample length.

4. The method according to claim 2, comprising photographing the rock sample while carrying out measurements taken while scratching the groove and while performing the micro-indentation test.

5. The method according to claim 1, further comprising measuring acoustic parameters of the rock sample and wherein determining mechanical parameters of the rock sample comprises determining a Poisson ratio of the rock sample.

6. The method according to claim 5, wherein the acoustic parameters include propagation velocities of compression and shear waves.

7. The method according to claim 5, comprising measuring the acoustic parameters of the rock sample within the groove created during the scratching step.

8. The method according to claim 5, wherein the rock sample is in the form of a core, the method comprising repeating measuring the acoustic parameters of the rock sample along the rock sample length.

9. The method according to claim 5, comprising photographing the rock sample while measuring the acoustic parameters of the rock sample.

10. The method according to claim 1, comprising recording microseismic emissions while scratching the groove and while performing the micro-indentation test.

11. A computer-readable medium having a program stored thereon, wherein the program comprises instructions to be executed while run on a computer system for determining mechanical parameters of a rock sample in which a groove has been scratched by causing a blade to advance at a constant speed and constant cutting depth along the rock sample in order to destroy a constant volume per unit of length at the surface of the rock sample, horizontal and vertical forces provided to the blade while scratching the groove being measured, and in which a micro-indentation test has been performed within the groove created by scratching the rock sample, wherein said instructions are adapted to cause the computer system to:

determine mechanical properties of the rock sample, determine at least one parameter chosen from among uniaxial compressive strength, angle of friction, internal cohesion, Brinell hardness, and Young's modulus of the rock sample.

12. A device for measuring geomechanical parameters of a rock sample, said device comprising:

a test bench intended for receiving a rock sample, a gantry whose movement along the rock sample is controlled and comprising micro-indentation and scratching instruments, said micro-indentation and scratching instruments comprising sensors to measure data during scratching and micro-indentations tests, the micro-indentation within a groove created by scratching the rock sample, a computer controlling the movement of the gantry along the rock sample, configured to receive data measured by the micro-indentation and scratching instruments attached to the gantry and comprising calculation means which use the data measured by the micro-indentation and scratching instruments attached to the gantry to determine at least one parameter among: the uniaxial compressive strength, angle of friction, internal cohesion, Brinell hardness, and Young's modulus of the rock sample.

13. The device according to claim 12, wherein the gantry further comprises an instrument for measuring acoustic parameters of the rock sample, and said computer is configured so that it also receives data measured by the instrument for measuring acoustic parameters of the rock sample and further comprises calculation means which allow using the data measured by the instrument for measuring acoustic parameters of the rock sample and the data measured by the micro-indentation and scratching instruments attached to the gantry to determine the Poisson's ratio of the rock sample, and said computer is further configured to record signals from the plurality of sensors for capturing acoustic emissions.

* * * * *